(12) United States Patent
Henderson

(10) Patent No.: US 8,050,937 B1
(45) Date of Patent: Nov. 1, 2011

(54) METHOD AND SYSTEM FOR PROVIDING RELEVANT CONTENT BASED ON CLAIM ANALYSIS

(75) Inventor: Kenneth J. Henderson, Folsom, CA (US)

(73) Assignee: Intuit Inc., Mountain View, CA (US)

( * ) Notice: Subject to any disclaimer, the term of this patent is extended or adjusted under 35 U.S.C. 154(b) by 1047 days.

(21) Appl. No.: 11/493,249

(22) Filed: Jul. 25, 2006

(51) Int. Cl.
*G06Q 10/00* (2006.01)
(52) U.S. Cl. ...................... 705/2; 705/3; 705/4
(58) Field of Classification Search .................. 705/2, 3, 705/4
See application file for complete search history.

(56) References Cited

U.S. PATENT DOCUMENTS

| | | | |
|---|---|---|---|
| 5,557,514 A * | 9/1996 | Seare et al. | 705/2 |
| 5,970,463 A * | 10/1999 | Cave et al. | 705/3 |
| 6,088,677 A * | 7/2000 | Spurgeon | 705/4 |
| 6,223,164 B1 * | 4/2001 | Seare et al. | 705/2 |
| 2004/0243441 A1 * | 12/2004 | Bocionek et al. | 705/2 |
| 2007/0055552 A1 * | 3/2007 | St. Clair et al. | 705/3 |

* cited by examiner

*Primary Examiner* — Gerald J. O'Connor
*Assistant Examiner* — Hiep V Nguyen
(74) *Attorney, Agent, or Firm* — Osha • Liang LLP (57) ABSTRACT

A method including receiving claim data corresponding to a subscriber from a health plan server, analyzing the claim data to select a medical code, and displaying health content related to the medical code.

21 Claims, 4 Drawing Sheets

METHOD AND SYSTEM FOR PROVIDING RELEVANT CONTENT BASED ON CLAIM ANALYSIS

BACKGROUND

People who are diagnosed with a new medical condition or who suffer from chronic or acute medical conditions typically want current, relevant information regarding treatments, medical research, support groups, etc. for these medical conditions. In addition, people receiving a new prescription medication typically want additional information regarding such things as the efficacy and potential side effects of the medication. Furthermore, people taking prescription medications to treat chronic conditions want current information regarding the availability and efficacy of alternative medications. People may also want current and relevant information regarding medical procedures and possible alternatives, and/or about medical service providers (e.g., physicians or hospitals). These people generally perform web searches attempting to find relevant and useful information regarding a medical condition, a medical procedure, a medical service provider, and/or a prescribed medication. To get valuable results, the searcher must determine the right keywords to use and sift through the results of the searches to find relevant information.

SUMMARY

In general, in one aspect, the invention relates to a method including receiving claim data corresponding to a subscriber from a health plan server, analyzing the claim data to select a medical code, and displaying health content related to the medical code.

In general, in one aspect, the invention relates to a graphical user interface that includes a claim management interface and an information interface. The claim management interface is configured to display a summary of claim data corresponding to the subscriber. The information interface is configured to display health content related to a medical code included in the claim data, wherein the medical code is selected by analyzing the claim data when the claim data is received in a claim management application.

In general, in one aspect, the invention relates to a claim management sentence including a subscriber system and a claim management application operatively connected to the subscriber system. The claim management application includes: a claim analysis component configured to analyze claim data received from a health plan server to select a medical code; and a graphical user interface configured to display health content related to the medical code on the subscriber system. The medical code may be any of: a diagnosis code, a drug code, a medical service provider code, and a medical procedure code In general, in one aspect, a computer usable medium includes computer readable program code embodied therein for causing a computer system to: receive claim data corresponding to a subscriber from a health plan server; analyze the claim data to select a medical code; and display health content related to the medical code.

Other aspects and benefits of the invention will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for providing relevant health content to a health plan subscriber based on diagnosis and drug information included in health plan claims. More specifically, in one or more embodiments of the invention, health plan claim data corresponding to a subscriber may be received from a health plan server. The received claim data is analyzed to select a diagnosis or prescribed drug from one or more diagnoses and prescribed drugs included in the claim data. A search is performed using keywords (or codes) associated with the selected diagnosis or prescribed drug to locate relevant health content available from various online health information sources. The relevant health content is then, upon request, displayed to the subscriber in a graphical user interface (GUI), possibly in conjunction with a summary of the claim data.

Figure 1:
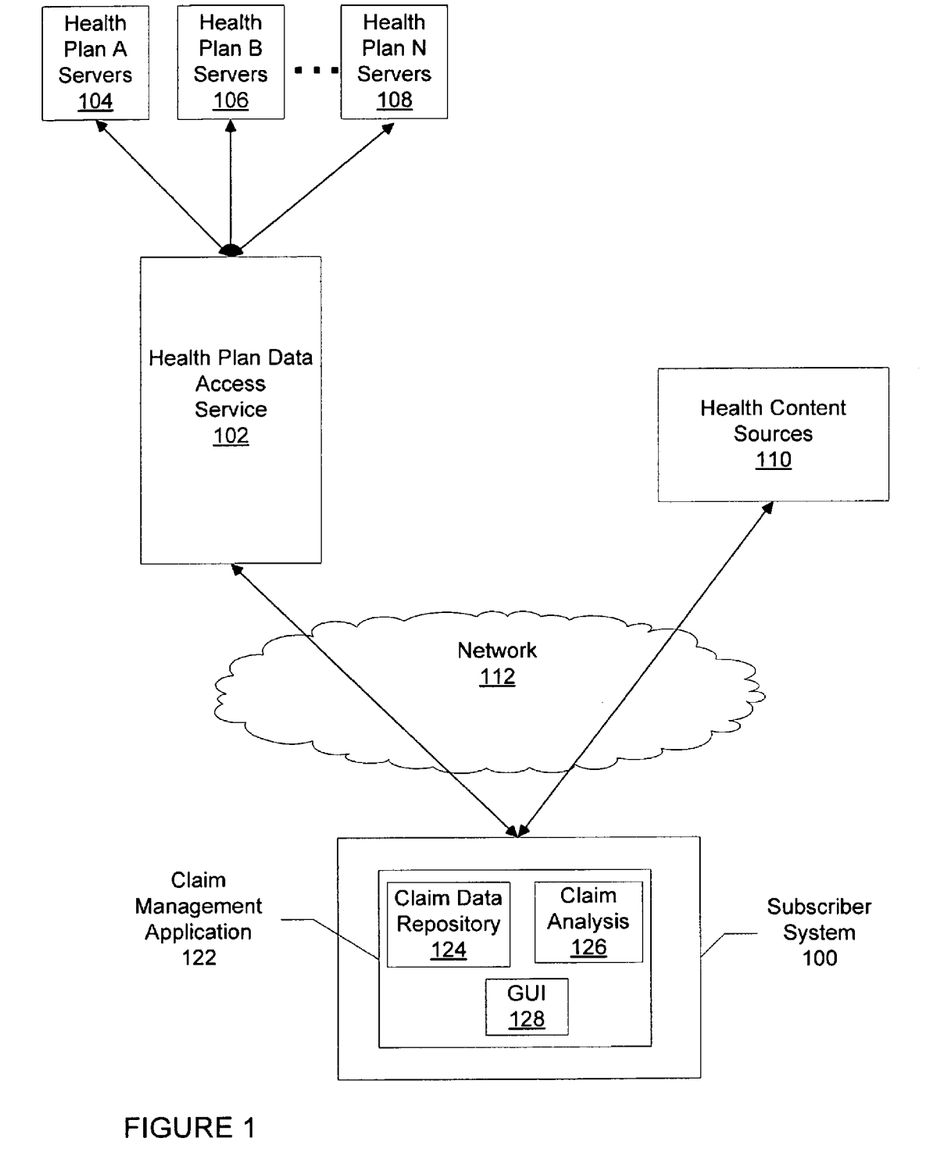
FIG. 1 shows a diagram of a system in accordance with one or more embodiments of the invention.

FIG. 1 shows a claim management system in accordance with one or more embodiments of the invention. In one embodiment of the invention, the claim management system includes one or more health plan servers (104-108), a health plan data access service (102), a subscriber system (100), and health content sources (110). While a single subscriber system is shown in the system of FIG. 1 for simplicity of presentation and explanation, one of ordinary skill will appreciate that multiple subscriber systems may be included. In some embodiments of the invention, the health plan servers (104-108) may be configured to communicate with the health plan data access service (102) via a network (e.g., a wide area network (WAN) such as the Internet, a wireless network, a local area network (LAN) or a combination of networks.) In one or more embodiments of the invention, the subscriber system (100) may be configured to communicate with the health plan data access server and the health content sources via a network (112). The network (112) may be a wide area network (WAN) such as the Internet, a wireless network, a local area network (LAN) or a combination of networks.

Each health plan server (104-108) is associated with a health plan provider (e.g., Aetna, United Healthcare, Humana, etc.) and may be configured to store claim data from benefit claims submitted by or on behalf of subscribers to one or more benefit plans included in a health plan provided by the health plan provider. A health plan server (104-108) may also be configured to store claim data from benefit claims submitted by or on behalf of covered family members of a subscriber.

In one or more embodiments of the invention, claim data for a submitted claim may include information required for consideration and payment of the claim such as a claim number or identifier, a subscriber identifier, the name of the person receiving a medical service or prescribed drug, information about the medical service(s) provided, a price of a medical service or included prescribed drug, medical service provider (e.g., a physician, hospital, clinic, pharmacy, etc.) identification information, etc. Claim data may also include information about one or more medical diagnoses and/or prescribed drugs. For example, claim data for a medical services claim covering a visit to a physician includes at least one diagnosis and may includes multiple diagnoses denoted as a primary diagnosis and secondary diagnoses. Claim data for a prescription drug claim submitted by a pharmacy includes information identifying the prescribed drug.

In one or more embodiments of the invention, claim data may be encoded using medical codes from Health Insurance Portability and Accountability Act (HIPAA) transaction and code sets. HIPAA is the federal law that establishes standards for the privacy and security of health information, as well as standards for electronic data interchange (EDI) of health information. The medical codes used may include codes from current approved versions of the Healthcare Common Procedure Coding System (HCPCS) codes, National Drug Codes (NDC), Current Procedure Terminology (CPT) codes, and International Classification of Disease (ICD) codes.

HCPCS is the code set used for reporting supplies, orthotic and prosthetic devices, and durable medical equipment. HPCS codes, in combination with the CPT codes, are also used to encode physician and other health care services. HCPCS codes also include medical codes for prescription drugs (i.e., drug codes). NDC is an alternative code set that may be used for coding prescription drugs and a few over-the-counter drugs. CPT codes (i.e., diagnosis codes) are used to describe health care services. ICD codes are used to describe diseases and other health problems (i.e., diagnoses).

Each health plan server (104-108) may be configured to allow a subscriber or an intermediary (e.g., health plan data access service (102)), with proper authentication, to download claim data corresponding to a subscriber. In some embodiments of the invention, the claim data corresponding to a subscriber includes claim data from both subscriber benefit claims and subscriber family member benefit claims. In one or more embodiments of the invention, the health plan server (104-108) is configured to authenticate a subscriber in accordance with the privacy and security requirements of HIPAA before allowing the download of the claim data associated with the subscriber in a manner known in the art.

In one or more embodiments of the invention, the health plan data access service (102) is configured to provide back-end services (e.g., storage and retrieval of information) to a claim management application (122) accessible by a subscriber using subscriber system (100). As is explained in more detail below, the health plan data access service is configured to accumulate claim data corresponding to a subscriber from each health plan server (104-108) storing such claim data and to send that claim data to the claim management application (122).

In one or more embodiments of the invention, the health plan data access service (102) may include one or more servers (not specifically shown) configured to provide the functionality of the health plan data access service. For example, one or more servers may be configured to import (i.e., download) and store claim data from the health plan servers (104-108), and/or one or more servers may be configured to manage network traffic between other servers in the health plan data access service (102) and subscriber systems (e.g., subscriber system (100)). In addition, as is explained in more detail below, in one embodiment of the invention, one or more servers in the health plan data access service (102) may be configured to host the claim management application (122) or one or more components (124), (126, 128) of the claim management application (122).

A subscriber system (100) may be a desktop computer, a laptop computer, a mobile device, such as a cell phone or personal digital assistant, or any other computing system suitable for using the claim management application (122). In one embodiment of the invention, the claim management application (122) may be installed on the subscriber system (100). In one or more embodiments of the invention, a subscriber may access the client management application (122) using a web browser, such as Internet Explorer, Mozilla, or Firefox; installed on the subscriber system. Furthermore, in some embodiments of the invention, the claim management application (122) may be downloaded from a health plan server 104-108 and installed on the subscriber system (100).

While the functionality and components of the claim management application (122) are shown in FIG. 1 and described herein as if the claim management application (122) is installed on the subscriber system (100), one of ordinary skill will appreciate other embodiments of the invention in which all or parts of the claim management application are hosted by the health data access service (102). For example, in one embodiment, the client management application (122) may be hosted by the health plan data access service (102) and accessed via a web browser installed on the subscriber system (100). In other embodiments of the invention, some components of the claim management application (122) may be hosted by the health plan data access service (102) (e.g., the claim data repository (124) or the claim analysis component (126)) while other components (e.g., the GUI (128)) are installed on the subscriber system 100.

In one or more embodiments of the invention, the claim management application includes a claim data repository (124), a claim analysis component (126), and a GUI (128). The claim data repository (124) is configured to store a subscriber's claim data received from one or more of the health plan servers (104-108) via the health plan data access service (102). In one or more embodiments of the invention, the claim data repository may be, for example, a database, a file system, one or more data structures configured in the memory of the subscriber system, or a suitable combination thereof.

In one or more embodiments of the invention, the GUI (128) is configured to prompt a subscriber to register with the health plan data access service (102). More specifically, in one or more embodiments of the invention, the GUI (128) is configured to receive registration information from the subscriber including the identity of the subscriber's health plans and the subscriber's authentication information for each health plan. In one or more embodiments of the invention, a subscriber's authentication information may include a subscriber's user identification and password for logging into a claim access interface (not specifically shown) of a heath plan server (104-108). The claim management application (122) is also configured to send the initial or subsequent registration information to the health plan data access service (102).

In one embodiment of the invention, the health plan data access service (102) is configured to receive and store the subscriber's registration information. In one or more embodiments of the invention, the health plan data access service is configured to submit the subscriber's authentication information to a health plan server (104-108) to gain access to claim data associated with the subscriber.

In some embodiments of the invention, the health plan data access service (102) is configured to import (i.e., download) claim data associated with the subscriber from each health plan server (104-108) associated with a health plan identified in the subscriber's registration information and store the claim data for subsequent download to the claim management application (122). In one or more embodiments of the invention, the health plan data access service (102) is configured to import only new claim data (i.e., claim data added to a health plan server (104-108) since the last time claim data was imported). In addition, in one or more embodiments of the invention, the health plan data access service (102) is configured to import claim data from the health plan servers (104-108) periodically (e.g., each night after midnight).

In one or more embodiments of the invention, the health plan data access service (102) is configured to send the imported claim data to the client management application (122). In one embodiment of the invention, the health plan data access service (102) and the client management application (122) are configured to automatically transfer the imported claim data, if any imported claim data is available, from the health plan data access service (102) to the claim management application (122) when the subscriber logs into the claim management application (122). In one embodiment of the invention, the health plan data access service (102) and the client management application (122) are configured to transfer the imported claim data, if any imported claim data is available, from the health plan data access service (102) to the claim management application (122) when the subscriber requests that the claim data be transferred. In one or more embodiments of the invention, the claim data is transferred in one or more protocols capable of transferring such data.

In one embodiment of the invention, the client management application (122) is configured to receive the claim data from the health plan data access service (102) and store the claim data in the claim data repository (124). In one or more embodiments of the invention, the claim analysis component (126) is configured to analyze the received claim data to identify diagnosis and prescription drug information included in the claim data. In one or more embodiments of the invention, the claim analysis component (126) may also be configured to identify medical service provider identification information or and/or information about the medical services provided. In one embodiment of the invention, the claim analysis component (126) is configured to analyze the claim data as the claim data is being received. In one embodiment of the invention, the claim analysis component (126) is configured to analyze the received claim data after the claim data is received and stored in the claim data repository (124).

In one more embodiments of the invention, the claim analysis component (126) is configured to identify diagnosis information, prescription drug information, medical service provider identification information, and/or information about the medical services provided by locating certain medical codes (i.e., diagnosis codes, drug codes, medical service provider codes, and/or medical procedure codes) in the received claim data. If multiple such medical codes are located, the claim analysis component (126) is further configured to prioritize the codes to select one of the codes. One of ordinary skill will appreciate that the claim analysis component (126) may be configured to use any suitable method of prioritization.

In one or more embodiments of the invention, the claim analysis component (126) may be configured to prioritize the medical codes using a frequency distribution over a period of time (e.g., three years). That is, each located code may be compared to claim data in the claim data repository to determine how many times that code has occurred in the claim data corresponding to the subscriber over a period of time and ranked based on the frequency of occurrence. In one embodiment of the invention, the code with the highest frequency of occurrence may be ranked the highest and the code with lowest frequency of occurrence may be ranked the lowest. The claim analysis component (126) may then select the highest ranked code (i.e., the one that has occurred most frequently) or the lowest ranked code (i.e., the one that has occurred least frequently or not at all) for further processing.

In some embodiments of the invention, the claim analysis component (126) may also use additional or different criteria to select a code for further processing, such as a relative importance (i.e., weight) of a medical code. For example, a diagnosis of cancer may be considered to be more important than a diagnosis of an ankle fracture. Similarly, a prescribed drug having a high likelihood of undesirable side affects may be considered to be more important than a prescribed drug having a low likelihood of side effects or a routine diagnosis. One of ordinary skill will appreciate that there are many different suitable ways to assign an important or weight to medical codes for purposes of prioritization.

In some embodiments of the invention, the claim analysis component (126) may be configured to maintain a data structure for use in prioritization that includes each diagnosis code, drug code, medical service provider code, and/or medical procedure code found in received claim data, the earliest date that the code was found, the latest data that the code was found, and the number of times the code has been included in previously received claim data. The data structure may also include an indicator of the relative importance of each of these medical codes. The data structure may be an array, a linked list, or any suitable data representation. The claim analysis component (126) may then use this data structure to determine the frequency distribution of the codes included in new claim data or for other prioritization methods.

In one embodiment of the invention, the claim analysis component (126) is configured to search for health content related to (i.e., relevant to) the selected medical code in the health content sources (110). In one or more embodiments of the invention, the health content sources (110) include web sites on the Internet. The web sites may include many varieties of health content including web feeds, chat rooms, blogs, static web pages, etc. In one or more embodiments, the health content sources (110) are validated, meaning a third party (i.e., a trusted physician, a pharmacist, a medical organization, etc.) has validated the contents.

In one embodiment of the invention, the claim analysis component (126) uses search criteria associated with the selected medical code to locate relevant health content available from the health content sources (110). In one embodiment of the invention, a data structure may be maintained that includes each diagnosis code, drug code, medical service provider code, and medical procedure code that may be used in encoding claim data along with search criteria for each code. In some embodiments of the invention, the search criteria may include one or more search keywords for each code. In some embodiments of the invention, the search criteria may also include one or more suggested web sites to be targeted in a search for related health content. The data structure may be any suitable representation such as a linked list, an array, etc. In one embodiment of the invention, the data structure may be included in the client management application (122). In other embodiments of the invention, the data structure may be stored on the heath plan data access service (102) and the claim analysis component (126) may be configured to request the search criteria associated with a selected code from the health plan data access service (102).

In one embodiment of the invention, once a code is selected, the claim analysis component (126) may use other medical codes in the claim data to determine the search criteria to be used to locate relevant health content. For example, if the selected code is a diagnosis code, search criteria associated with the medical procedures performed as a result of the diagnosis may used in conjunction with search criteria for the diagnosis code to locate health content related to the diagnosis and to post-procedure recommendations (e.g., diet, physical therapy, etc.) and possible alternative procedures or therapies.

In some embodiments of the invention, if the selected code is a medical service provider code, the claim analysis component (126) may use search criteria to locate rating information (e.g., poor, good, better, best) related to the medical service provider, where the medical service provider is rated against an industry standard and against other physicians in the health plan medical service provider network.

In one embodiment of the invention, the claim analysis component (126) is configured to use a search engine available on the Internet (e.g., Google, Teoma, Altavista, Lycos, etc.) that performs the search using search criteria provided by the claim analysis code (126) and ranks the search results. In other embodiments of the invention, the claim analysis component (126) may be configured to use a search engine hosted by the health plan data access service (102) that is specifically configured to locate and rank health content available from the health content sources (110). One of ordinary skill will appreciate that many different approaches may be used to search for health content provided by the health content sources (110) and to rank the results of the search that are included within the scope of the invention.

In one or more embodiments of the invention, the claim analysis component (126) is configured to provide the relevant health content (i.e., the search results) to the GUI (128) for display. In some embodiments of the invention, the claim analysis component (126) provides the relevant health content in the form of links to the relevant health content derived from the search results. In some embodiments of the invention, the claim analysis component (126) may be configured to analyze the search results to locate web feeds and to enroll the subscriber to receive one or more of the web feeds.

Figure 2:
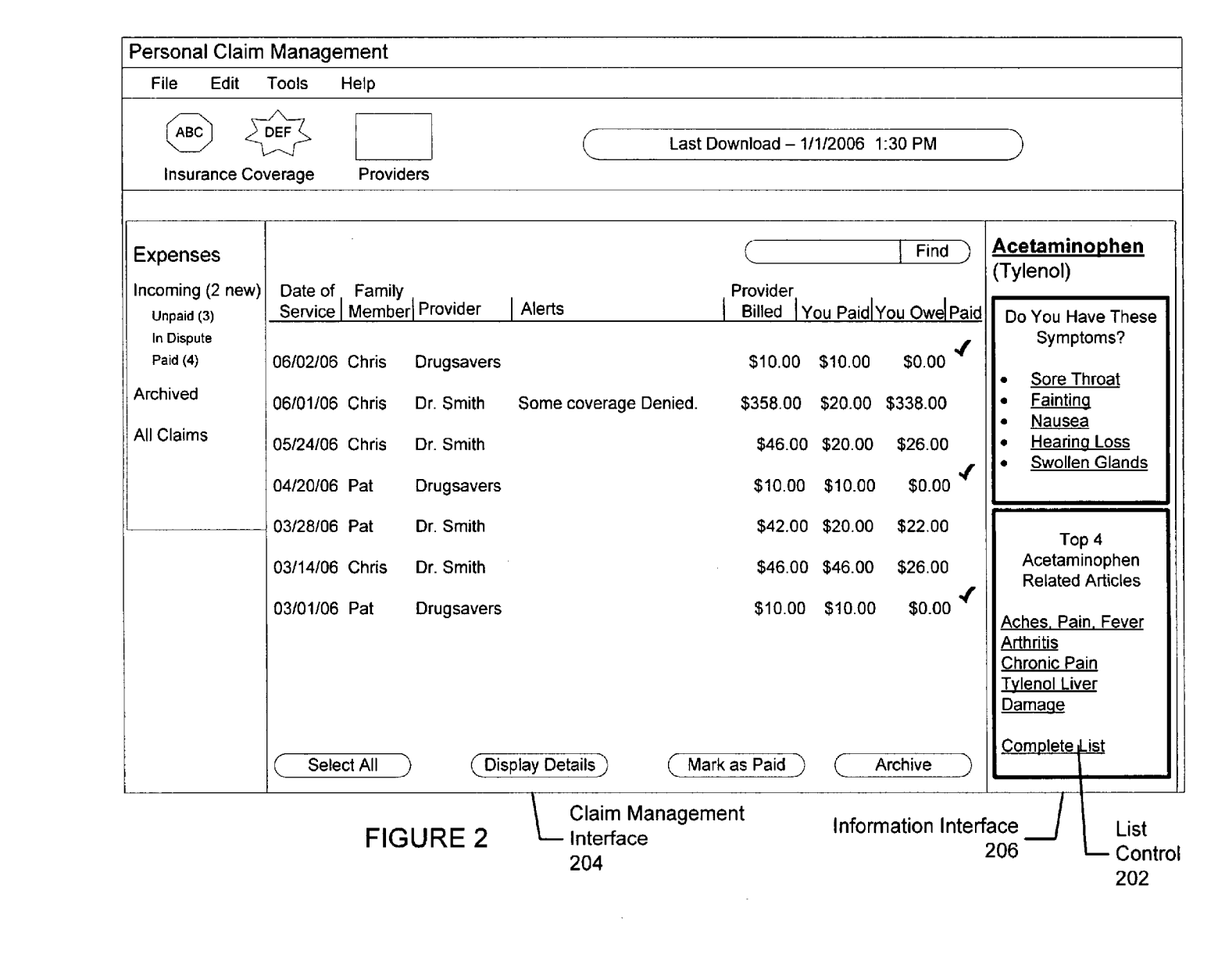
FIG. 2 shows an illustrative representation of a user interface displaying relevant content in accordance with one or more embodiments of the invention.

In one embodiment of the invention, the GUI (128) is configured to provide an interface (via the subscriber system (100)) for viewing and managing claim data stored in the claim data repository (124). More specifically, in one embodiment of the invention, the GUI (128) is configured to display a summary of claim data stored in the claim data repository (124) and the relevant health content provided by the claim analysis component (126). FIG. 2 shows an example of a screen display provided by the GUI (128) in accordance with one or more embodiments of the invention. In one embodiment of the invention, the GUI (128) is configured to display a claim management interface (204) and an information interface (206) as a single screen display. In other embodiments of the invention, the GUI (128) may be configured to display the information interface as a separate screen display that a subscriber may access by selecting a control configured in the claim management interface (204). The claim management interface (204) includes the summary of the claim data and the information interface (206) presents the relevant health content in the form of links to the content. In one or more embodiments of the invention, the GUI (128) is configured to display a small number of the top ranked links (e.g., five links) and the information interface (206) includes a list control (202) configured to allow the subscriber to view the remainder of the links.

Figure 3:
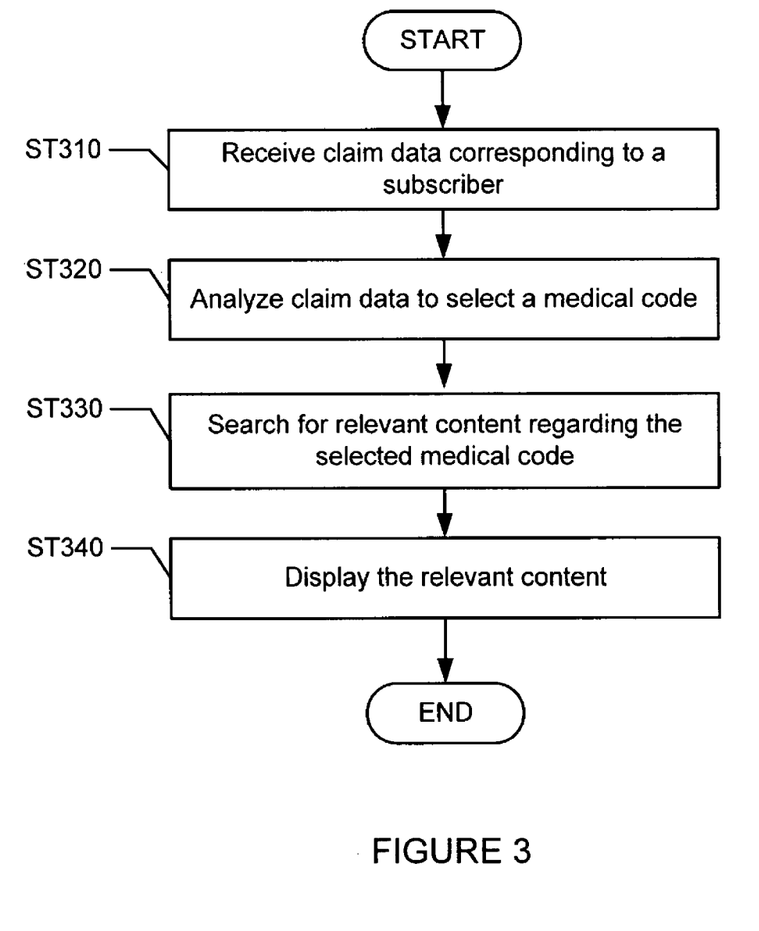
FIG. 3 shows a flowchart in accordance with one or more embodiments of the invention.

FIG. 3 shows a flowchart of a method for providing relevant health content to subscriber based on analysis of benefit claims submitted to a health plan provider by or on behalf of a subscriber and/or members of the subscriber's family in accordance with one or more embodiments of the invention. While the various steps in this flowchart are presented and described sequentially, one of ordinary skill will appreciate that some or all of the steps may be executed in different orders and some or all of the steps may be executed in parallel.

As shown in FIG. 3, claim data corresponding to a subscriber is received by the subscriber's claim management application (ST310) from the health plan data access service. In one or more embodiments, the health plan data access service periodically imports the claim data corresponding the subscriber from the servers of the health plans providing benefits to the subscriber. This claim data may be automatically transferred to the claim management application by the health plan data access service when the subscriber logs into the claim management application. Alternatively, the subscriber may log into the claim management application and request that the claim data be transferred.

The received claim data is analyzed by the claim management application to select a diagnosis, a prescribed drug, a medical service provider, or a medical procedure (ST320). More specifically, the claim analysis component analyzes the received claim data to locate any diagnosis codes, drug codes, medical serviced provider codes, and/or medical procedure codes in the claim data and prioritizes the codes to select one. Prioritization methods that may be used in embodiments of the invention to select a code have been previously described.

Once a medical code has been selected, a search is performed to locate relevant health content regarding the diagnosis, prescribed drug, medical service provider, and/or medical procedure corresponding to the code (ST330). More specifically, in some embodiments of the invention, the claim analysis component uses a search engine and search criteria (e.g., keywords) corresponding to the selected medical code to find relevant health content on appropriate health content sources accessible via the Internet. In one embodiment of the invention, if the relevant health content includes a web feed, the claim analysis component may enroll the subscriber to receive the web feed.

After the relevant heath content is found, the relevant health content is displayed to the subscriber in a graphical user interface of the claim management application (ST340). In some embodiments, the relevant heath content is displayed in the form of a list of links to the content that the subscriber may select to access the content. The claim management application may display the relevant health content to the subscriber automatically in conjunction with a summary of the received claim data. Alternatively, the subscriber may select a control in the GUI of the claim management application to view a display of the relevant health content.

Those skilled in the art will appreciate that in one or more embodiments, the invention provides a subscriber with health content related to a diagnosis, a prescribed drug, a medical procedure, or a medical service provider without requiring the subscriber to search for the health content. Furthermore, in one or more embodiments of the invention, the health content is displayed to the subscriber in conjunction with a summary of the subscriber's health benefit claims, one of which may include the diagnosis, prescription drug, medical procedure, or medical service provider.

Figure 4:
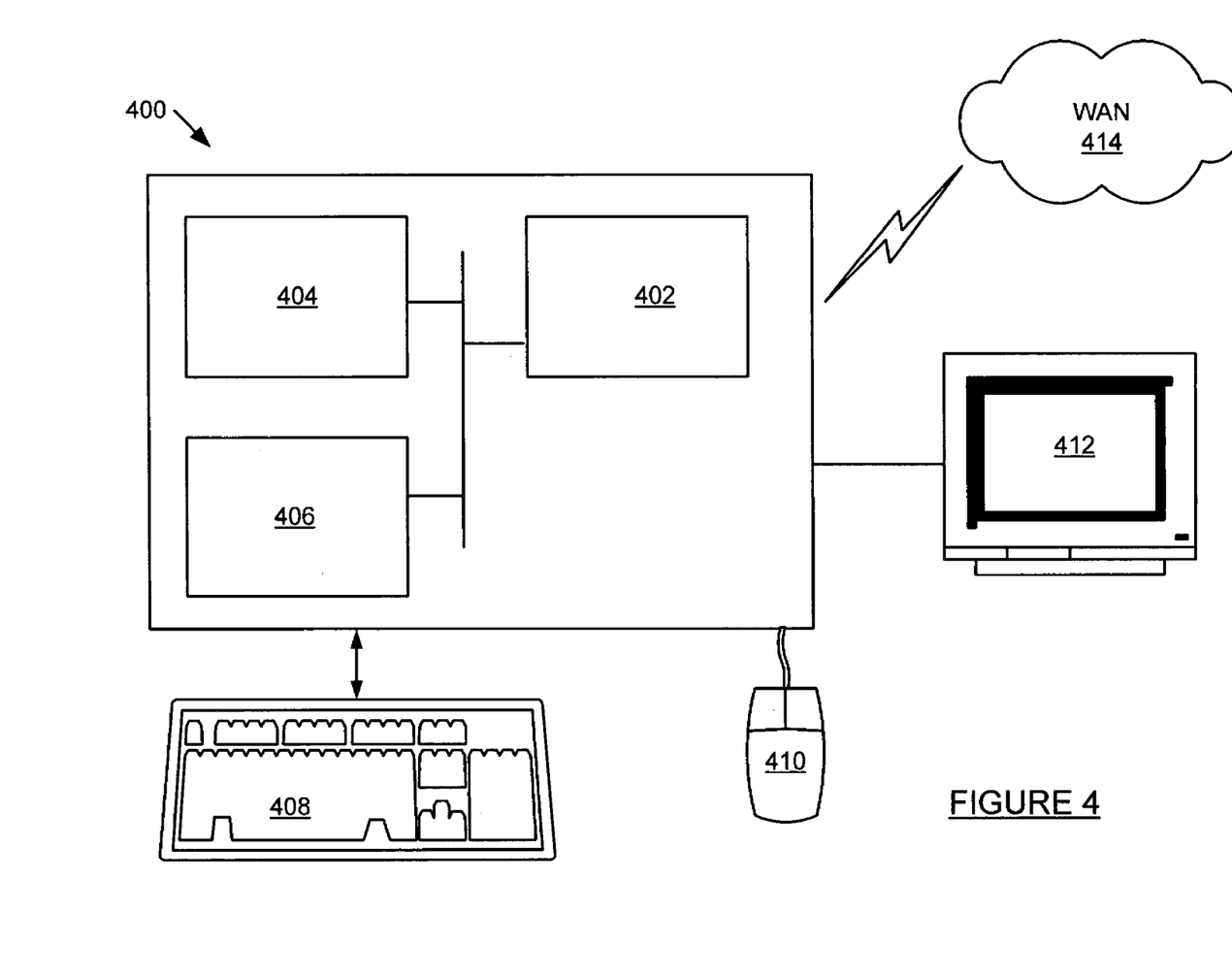
FIG. 4 shows a diagram of a computer system in accordance with one or more embodiments of the invention.

The invention may be implemented on virtually any type of computer regardless of the platform being used. For example, as shown in FIG. 4, a computer system (400) includes a processor (402), associated memory (404), a storage device (406), and numerous other elements and functionalities typical of today's computers (not shown). The computer (400) may also include input means, such as a keyboard (408) and a mouse (410), and output means, such as a monitor (412). The computer system (400) may be connected to a local area network (LAN) or a wide area network (e.g., the Internet) (not shown) via a network interface connection (not shown). Further, the computer system (400) may be a mobile device connected to a wireless connection. Those skilled in the art will appreciate that these input and output means may take other forms.

Further, those skilled in the art will appreciate that one or more elements of the aforementioned computer system (400) may be located at a remote location and connected to the other elements over a network. Further, the invention may be implemented on a distributed system having a plurality of nodes, where each portion of the invention may be located on a different node within the distributed system. In one or more embodiments of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method, comprising:
    downloading, by a claim management application (CMA) executing on a processor of a computer system and operated by a party selected from a group consisting of a patient and a family member of the patient, a plurality of claim data items corresponding to the patient from a health plan server;
    identifying, by the CMA operated by the party, a plurality of medical codes within the plurality of claim data items;
    determining, by the CMA operated by the party, a plurality of priorities for the plurality of medical codes based on a number of times that each of the medical codes in the plurality of medical codes is found in claim data previously downloaded to the CMA operated by the party over a pre-determined period of time;
    selecting, by the CMA operated by the party, a medical code from the plurality of medical codes based on the plurality of priorities;
    identifying, by the CMA operated by the party, a search criterion corresponding to the medical code;
    searching, based on the search criterion, a health content source operatively connected to the CMA by an electronic network;
    obtaining, by the CMA and in response to searching the health content source, a medical recommendation related to the medical code from the health content source; and
    displaying the medical recommendation within an information interface of the CMA.

2. The method of claim 1, wherein the medical code is one selected from the group consisting of a diagnosis code, a drug code, a medical service provider code, and a medical procedure code.

3. The method of claim 1, wherein the medical recommendation identified at least one selected from a group consisting of a therapy and a diet.

4. The method of claim 1, wherein displaying health content further comprises subscribing the subscriber to a web feed comprising a portion of the medical recommendation.

5. The method of claim 1, further comprising displaying a summary of the claim data in a claim management interface of the claim management application.

6. The method of claim 1, wherein determining the priority ranking of the one or more medical codes is further based on a pre-determined importance measure of each of the one or more medical codes.

7. The method of claim 1, wherein the medical code has a lowest frequency of occurrence among the one or more medical codes found in the previously received claim data over the pre-determined period of time.

8. The method of claim 1, wherein the medical code has a highest frequency of occurrence among the one or more medical codes found in the previously received claim data over the pre-determined period of time.

9. The method of claim 1, wherein receiving the claim data comprises automatically receiving the claim data in the claim management application when the subscriber logs into the claim management application.

10. A non-transitory computer usable medium comprising computer readable program code embodied therein for causing a computer system to display a graphical user interface (GUI), the GUI comprising:
    a claim management interface configured to display, to a party selected from a group consisting of a patient and a family member of the patient, a summary of a plurality of claim data items corresponding to the patient; and
    an information interface configured to display, to the party, a medical recommendation related to a medical code of a plurality of medical codes identified in the plurality of claim data items,
    wherein the non-transitory computer usable medium further comprises computer readable program code embodied therein for causing the computer system to obtain the medical recommendation by:
    identifying the plurality of medical codes within the plurality of claim data items;
    determining a plurality of priorities for each of the medical codes in the plurality of medical codes based on a number of times that each of the plurality of medical codes is found in claim data previously downloaded over a pre-determined period of time;
    selecting the medical code from the plurality of medical codes based on the plurality of priorities;
    identifying a search criterion corresponding to the medical code; and
    searching, based on the search criterion, a health content source operatively connected to the GUI using an electronic network.

11. The non-transitory computer usable medium of claim 10, wherein the medical code is one selected from a group consisting of a diagnosis code, a drug code, a medical service provider code, and a medical procedure code.

12. The non-transitory computer usable medium of claim 10, the medical recommendation identifies at least one selected from a group consisting of a therapy or a diet.

13. A claim management system comprising:
   a hardware processor;
   a claim data repository storing a plurality of claim data items for a patient downloaded from a health care server;
   a claim analysis component executing on the hardware processor, operated by a party selected from a group consisting of the patient and a family member of the patient, and configured to:
      identify, within the plurality of claim data items, a plurality of medical codes;
      determine a plurality of priorities for each of the medical codes in the plurality of medical codes based on a number of times that each of the plurality of medical codes is found in claim data previously downloaded over a pre-determined period of time;
      select a medical code from the plurality of medical codes based on the plurality of priorities;
      identify a search criterion corresponding to the medical code;
      search, based on the search criterion, a health content source operatively connected to the claim analysis component by an electronic network; and
      obtain, in response to searching the health content source, a medical recommendation related to the medical code; and
   a graphical user interface (GUI) executing on the hardware processor and configured to display the medical recommendation related to the medical code to the party,
   wherein the medical code is one selected from the group consisting of a diagnosis code, a drug code, a medical service provider code, and a medical procedure code.

14. The claim management system of claim 13, wherein the medical recommendation identifies at least one selected from a group consisting of a therapy and a diet.

15. The claim management system of claim 13, further comprising a health plan data access service configured to:
   import the plurality of claim data items from the health plan server; and
   send the plurality of claim data items to the claim data repository.

16. The claim management system of claim 13, wherein the GUI is further configured to display a claim management interface comprising a summary of the claim data to the party and an information interface comprising the medical recommendation to the party.

17. A non-transitory computer usable medium comprising computer readable program code embodied therein for causing a computer system to:
   download a plurality of claim data items corresponding to a patient from a health plan server to a claim management application (CMA) operated by a party selected from a group consisting of the patient and a family member of the patient;
   identify a plurality of medical codes within the plurality of claim data items downloaded to the CMA operated by the party;
   determine a plurality of priorities for the plurality of medical codes based on a number of times that each of the medical codes in the plurality of medical codes is found in claim data previously downloaded to the CMA operated by the party over a pre-determined period of time;
   select a medical code from the plurality of medical codes based on the plurality of priorities;
   identify a search criterion corresponding to the medical code;
   search, based on the search criterion, a health content source operatively connected to the CMA using an electronic network;
   obtain, in response to searching the health content source, a medical recommendation related to the medical code from the health content source; and
   display the medical recommendation related to the medical code within a graphical user interface (GUI) of the CMA operated by the party.

18. The non-transitory computer usable medium of claim 17, wherein the medical code is one selected from the group consisting of a diagnosis code, a drug code, a medical service provider code, and a medical procedure code.

19. The non-transitory computer usable medium of claim 17, wherein the medical recommendation identifies at least one selected from a group consisting of a therapy or a diet.

20. The non-transitory computer usable medium of claim 17, wherein the computer readable program code to display health content further comprises computer readable program code to subscribe the user to a web feed comprising a portion of the health content.

21. The non-transitory computer usable medium of claim 17, wherein the computer readable program code to prioritize the plurality of medical codes further comprises computer readable program code to cause the computer system to prioritize the plurality of medical codes based on a pre-determined importance measure of each medical code in previously received claim data stored in a claim data repository.

* * * * *